(12) United States Patent
Al-Ali et al.

(10) Patent No.: US 9,195,385 B2
(45) Date of Patent: Nov. 24, 2015

(54) PHYSIOLOGICAL MONITOR TOUCHSCREEN INTERFACE (71) Applicant: MASIMO CORPORATION, Irvine, CA (US)

(72) Inventors: Ammar Al-Ali, San Juan Capistrano, CA (US); Bilal Muhsin, San Clemente, CA (US); Keith Indorf, Riverside, CA (US)

(73) Assignee: Masimo Corporation, Irvine, CA (US)

( * ) Notice: Subject to any disclaimer, the term of this patent is extended or adjusted under 35 U.S.C. 154(b) by 300 days.

(21) Appl. No.: 13/850,000

(22) Filed: Mar. 25, 2013

(65) Prior Publication Data

US 2013/0254717 A1 Sep. 26, 2013

Related U.S. Application Data (60) Provisional application No. 61/615,307, filed on Mar. 25, 2012, provisional application No. 61/615,316, filed on Mar. 25, 2012, provisional application No. 61/615,876, filed on Mar. 26, 2012.

(51) Int. Cl.
G06F 3/14 (2006.01)
G06F 3/0485 (2013.01)
(Continued)

(52) U.S. Cl.
CPC ............ *G06F 3/0485* (2013.01); *G06F 3/0482* (2013.01); *G06F 3/0486* (2013.01);
(Continued)

(58) Field of Classification Search
CPC ..................................... G06F 3/14; G06F 3/17

USPC .......................................... 715/728, 733, 830
See application file for complete search history.

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

EP 1965324 A1 9/2008
EP 2112594 A2 10/2009

OTHER PUBLICATIONS

"Configuring the Microphones Using AP-Ware," Feb. 17, 2009. Retrieved Jun. 5, 2013, <http://web.archive.org/web/20090217190928/http://www.accessgrid.org/agdp/howto/config-genter-ap400/1.5.1/html/x430.html>.
(Continued)

*Primary Examiner* — Ruay Ho
(74) *Attorney, Agent, or Firm* — Knobbe Martens Olson & Bear LLP (57) ABSTRACT A physiological monitor touchscreen interface which presents interface constructs on a touchscreen display that are particularly adapted to finger gestures. The finger gestures operate to change at least one of a physiological monitor operating characteristic and a physiological touchscreen display characteristic. The physiological monitor touchscreen interface includes a first interface construct operable to select a menu item from a touchscreen display and a second interface construct operable to define values for the selected menu item. The first interface construct can include a first scroller that presents a rotating set of menu items in a touchscreen display area and a second scroller that presents a rotating set of thumbnails in a display well. The second interface construct can operate to define values for a selected menu item.

9 Claims, 9 Drawing Sheets (51) Int. Cl.
*G06F 3/0488* (2013.01)
*G06F 3/0482* (2013.01)
*G06F 3/0484* (2013.01)
*G06F 3/0486* (2013.01)
*G06F 19/00* (2011.01)

(52) U.S. Cl.
CPC .......... *G06F3/0488* (2013.01); *G06F 3/04845* (2013.01); *G06F 3/04847* (2013.01); *G06F 19/3406* (2013.01)

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |

(56) References Cited

U.S. PATENT DOCUMENTS

| | | |
|---|---|---|
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,374,535 B2 | 5/2008 | Schoenberg et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |

(56) References Cited

U.S. PATENT DOCUMENTS

| | | |
|---|---|---|
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 2009/0019401 A1 | 1/2009 | Park et al. |
| 2011/0317192 A1 | 12/2011 | Fukuoka et al. |
| 2012/0026119 A1 | 2/2012 | Judy et al. |
| 2013/0036357 A1* | 2/2013 | Hendrickson ................. 715/728 |
| 2013/0185642 A1* | 7/2013 | Gammons ..................... 715/733 |

OTHER PUBLICATIONS

International Search Report and Written Opinion for PCT/US2013/033762, mailed Jun. 13, 2013, in 12 pages.

* cited by examiner

PHYSIOLOGICAL MONITOR TOUCHSCREEN INTERFACE

CROSS-REFERENCE TO RELATED APPLICATIONS

The present application claims priority benefit under 35 U.S.C. §119(e) to U.S. Provisional Patent Application Ser. No. 61/615,307, filed Mar. 25, 2012, titled Physiological Monitor User Controls; U.S. Provisional Patent Application Ser. No. 61/615,316, filed Mar. 25, 2012, titled Physiological Monitor User Interface; and U.S. Provisional Patent Application Ser. No. 61/615,876, filed Mar. 26, 2012, titled Physiological Monitor Touchscreen; all of the above referenced applications are hereby incorporated in their entireties by reference herein.

BACKGROUND OF THE INVENTION

Pulse oximetry is a widely accepted noninvasive procedure for measuring the oxygen saturation level of arterial blood, an indicator of a person's oxygen supply. A typical pulse oximetry system utilizes an optical sensor attached to a fingertip to measure the relative volume of oxygenated hemoglobin in pulsatile arterial blood flowing within the fingertip. Oxygen saturation ($SpO_2$), pulse rate and a plethysmograph waveform, which is a visualization of pulsatile blood flow over time, are displayed on a monitor accordingly.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated in their entirety by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated in their entirety by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Cercacor Laboratories, Inc., Irvine, Calif. (Cercacor) and all incorporated in their entirety by reference herein. Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad87™ and Rad57™ monitors, all available from Masimo. Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY OF THE INVENTION

A physiological monitor touchscreen interface presents interface constructs on a touchscreen display that are particularly adapted to finger gestures so to change at least one of a physiological monitor operating characteristic and a physiological touchscreen display characteristic. The physiological monitor touchscreen interface has a first interface construct operable to select a menu item from a touchscreen display and a second interface construct operable to define values for the selected menu item.

In various embodiments, the first interface construct has a first scroller that presents a rotating set of the menu items in a touchscreen display area and a second scroller that presents a rotating set of thumbnails in a display well. The thumbnails reference the menu items and the thumbnails rotate with the menu items. The first scroller presents a rotating set of second level menu items upon selection of the menu item. The second interface construct is a slider for selecting limits for one of the second level menu items. A spinner is used in conjunction with the slider for making a first gross limit selection with the slider followed by a finer limit selection with the spinner. A parameter area displays parameter values in a full presentation format and a parameter well area displays parameter values in a abbreviated presentation format. The full presentation format is a larger font that the abbreviated presentation format. A dynamic space allocation for the parameters values is presented in the parameter area such that the more parameters there are in the parameter area and, accordingly, the fewer parameters there are in the parameter well area, then the larger the display font for the parameters in the parameter area.

BRIEF DESCRIPTION OF THE DRAWINGS

FIGS. 2-7 are illustrations of various touchscreen interface constructs for controlling a physiological monitor;

FIG. 6 is an illustration of a slider-spinner; and

DETAILED DESCRIPTION OF THE PREFERRED EMBODIMENTS

Figure 1:
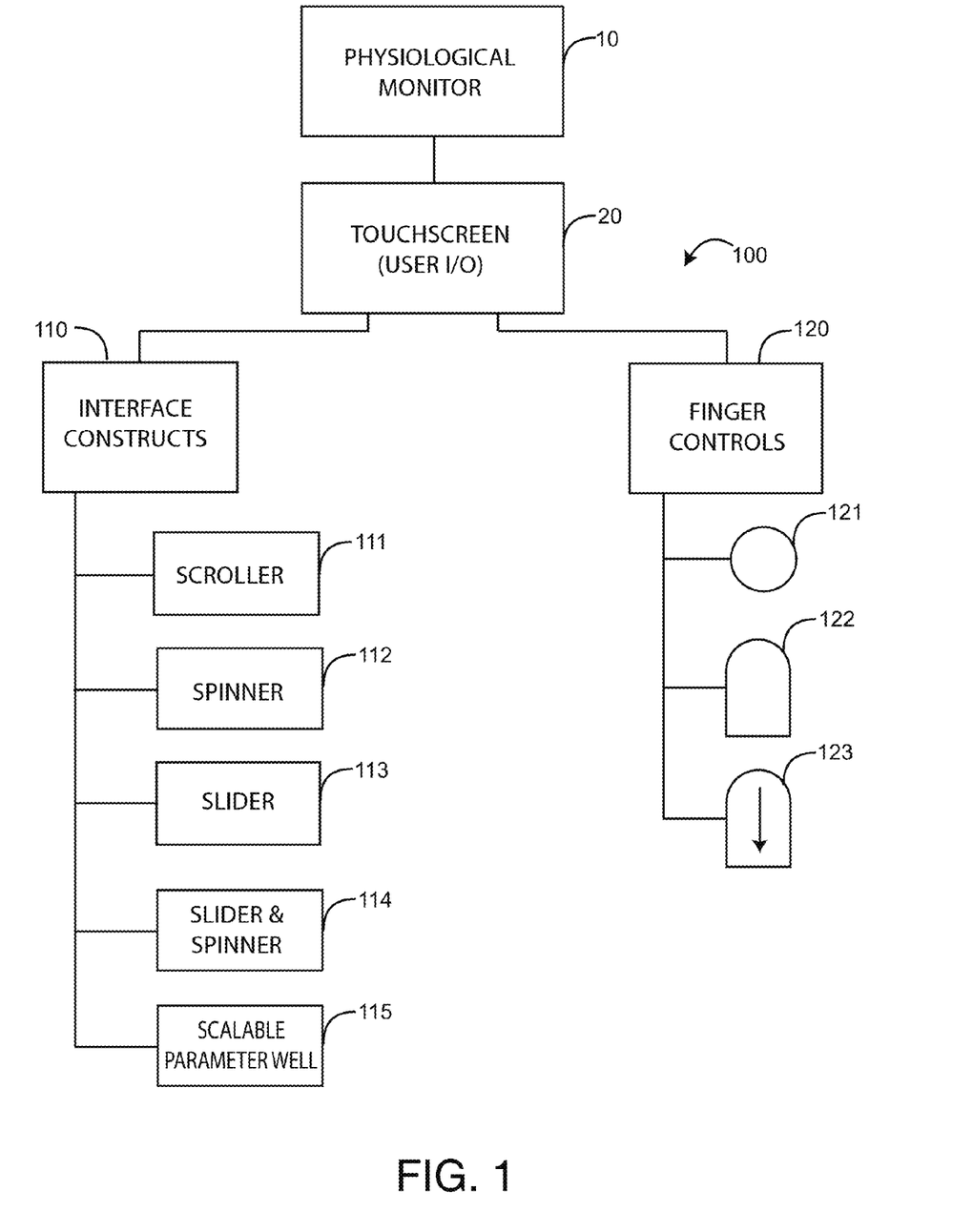
FIG. 1 is a hierarchical chart of a physiological monitor touchscreen interface including interface constructs and finger controls.

FIG. 1 illustrates a touchscreen interface 100 for a physiological monitor 10 and, in particular, for a touchscreen display 20 integral to the monitor 10. In general, the touch screen interface 100 provides an intuitive, gesture-oriented control for the physiological monitor 10. In particular, the touch-screen display 20 presents a user with interface constructs 110 responsive to finger controls 120 so as to change displays and settings, such as monitor operating characteristics, display contents and display formats using a finger touch, a finger touch and move, or a fingertip flick.

As shown in FIG. 1, interface constructs 110 include a scroller 111, a spinner 112, a slider 113, a slider-spinner 114 and a scalable parameter well 115. A scroller 111 is described below with respect to FIGS. 2-3. A spinner 112 is described below with respect to FIGS. 4A-C. A slider 213 is described below with respect to FIGS. 2-3. A slider-spinner 214 is described below with respect to FIGS. 5A-B. A scalable parameter well 216 is described below with respect to FIGS. 7A-D.

Also shown in FIG. 1, finger controls 120 include a touch 121, a touch and move 121 and a flick 121. A touch 121 is finger contact with an active display area. A touch and move 121 is finger contact in conjunction with finger movement in a particular direction. A flick 121 is finger contact in conjunction with a quick finger movement in a particular direction.

FIGS. 2-7 illustrate various touchscreen interface constructs 110 (FIG. 1) for controlling a physiological monitor 10 (FIG. 1), as described above. FIGS. 2A-D illustrate a scroller 200 construct configured for a touchscreen display. The scroller 200 is organized as a menu 210 disposed on a virtual, horizontally-rotatable loop. Only a viewable section 201-204 of the menu 210 is visible on the display at any given time. The scroller 200 is responsive to finger controls so as to bring into view any menu section, as described below.

Also shown in FIGS. 2A-D, a scroller 200 embodiment has thumbnails 250 disposed on a second, virtual, horizontally-rotatable loop located in a display well 211. The menu 210 has menu icons 230 and corresponding menu titles 240. The thumbnails 250 have a one-to-one correspondence to the menu icons 230, as indicated by thumbnail icons corresponding to the menu icons or thumbnail initials corresponding to the menu titles 240.

Further shown in FIGS. 2A-D, the scroller 200 advantageously allows for an unrestricted number of menu items. A user can rotate the scroll left or right using touch and move 122 (FIG. 1). A user can scroll left or right with velocity using flick 123 (FIG. 1). Further, a user can navigate to a menu item using touch 121 (FIG. 1) on menu item icon or title. In addition, a user can quick scroll to menu item using touch 121 (FIG. 1) on a thumbnail in the display well 211.

As shown in FIGS. 2A-D, when the user applies touch and move 207 (FIG. 2A) to the menu icons the user can freely and smoothly slide the menu 201 (FIG. 2A) to the left 202 (FIG. 2B) or the right. On release the menu icons snap and lock 203 (FIG. 2C) to their closest grid location employing an ease-in animation so the transition is smooth and natural and not abrupt. Then, on touch 208 (FIG. 2C) the user can navigate to any visible menu option 210. The navigate executes on release.

Figure 2A:
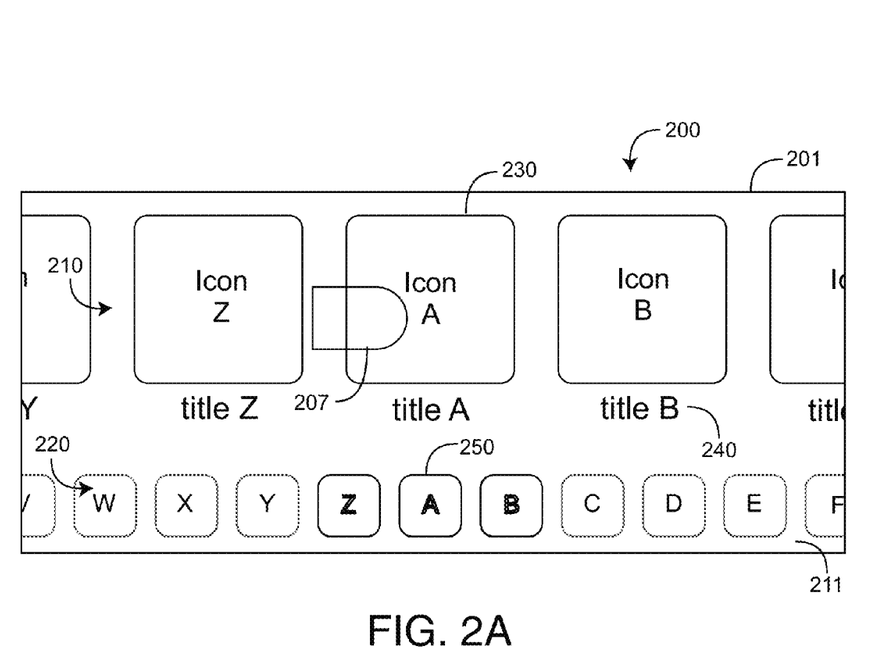
FIGS. 2A-D are illustrations of a scroller.
Figure 2B:
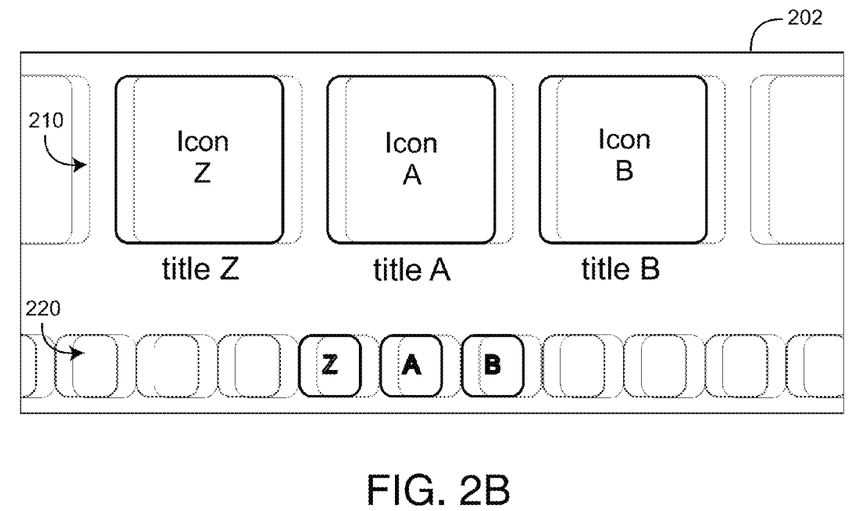
Figure 2C:
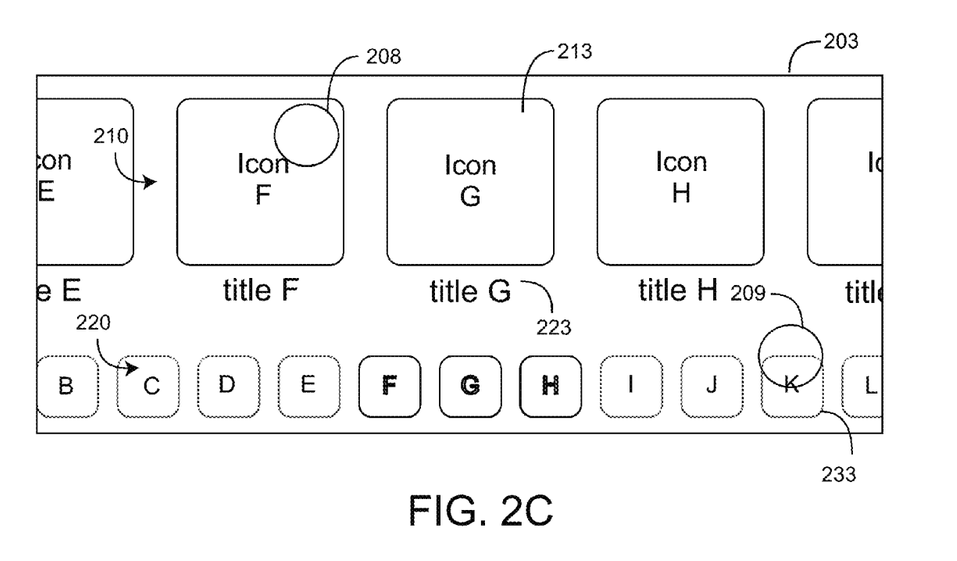
Figure 2D:
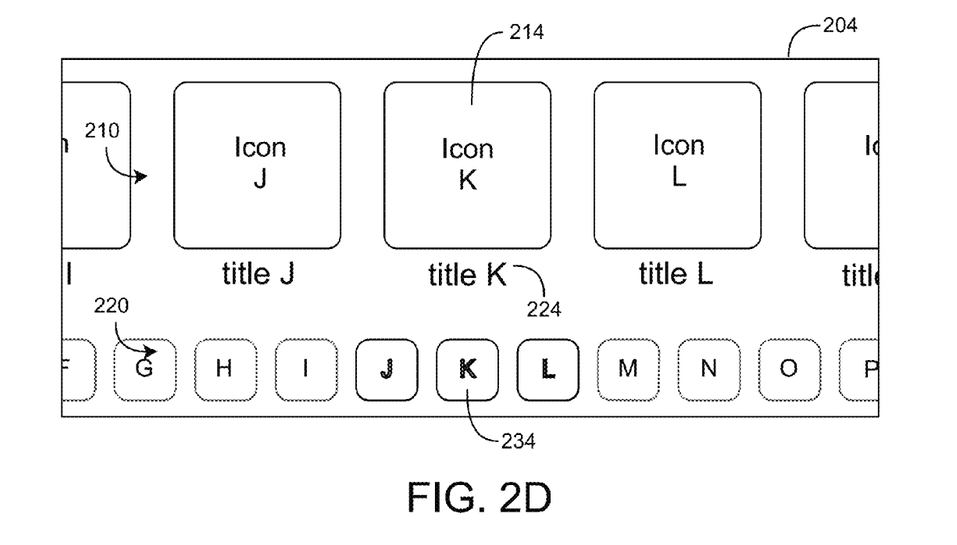

Further shown in FIGS. 2C-D, when the user wants to jump to a menu item not on the screen they can use a quick scroll. The user applies touch 209 (FIG. 2C) on a particular thumbnail indicator (K) 233 and the icon menus scroll into position giving center focus to the menu item (Icon K) 214 FIG. 2D represented by the touched thumbnail indicator 233. As shown in FIG. 2D, once the icon menu scroll animation is complete, the thumbnail indicators rapidly slide to their new orientation.

When the user applies flick (not shown) to the menu icons 210, the menu icons move with velocity along the horizontal vector the gesture implied and the icon menus slide into place. In particular, when the menu icons momentum decreases and they begin to come to a stop, the menu icons will snap to their closest grid location as described above.

Figure 3A:
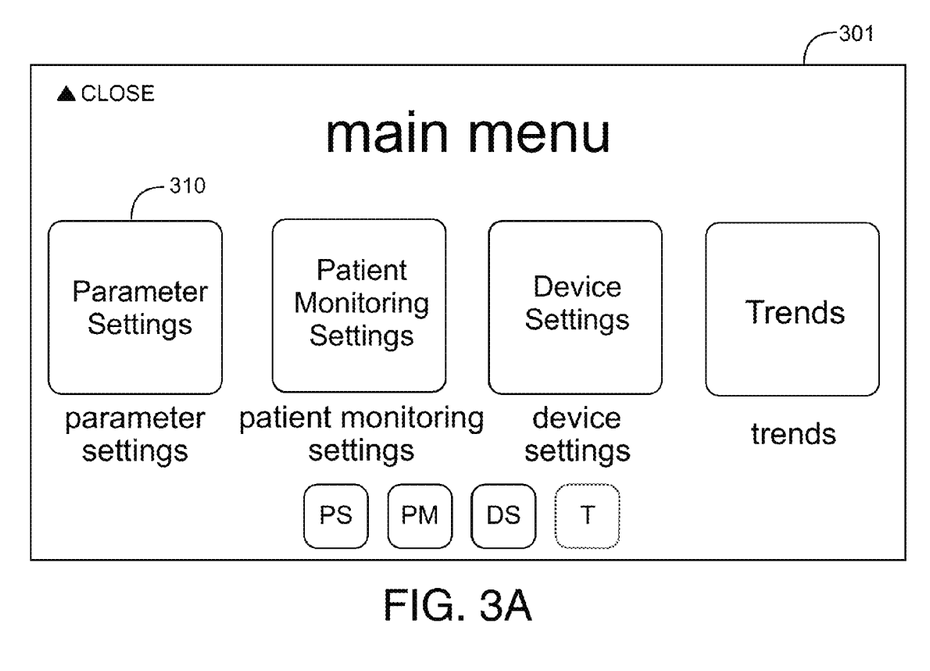
FIGS. 3A-C are illustrations of a physiological monitor main menu and sub-menus implemented with a scroller.
Figure 3B:
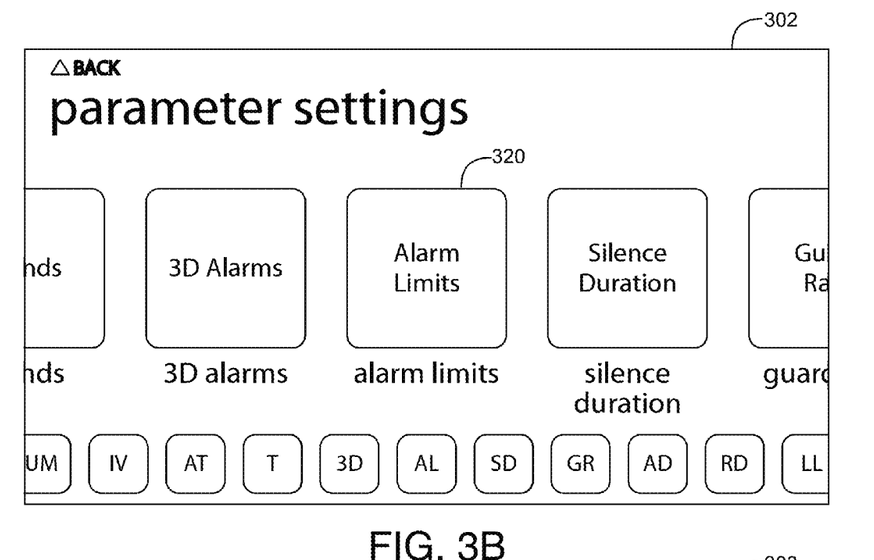
Figure 3C:
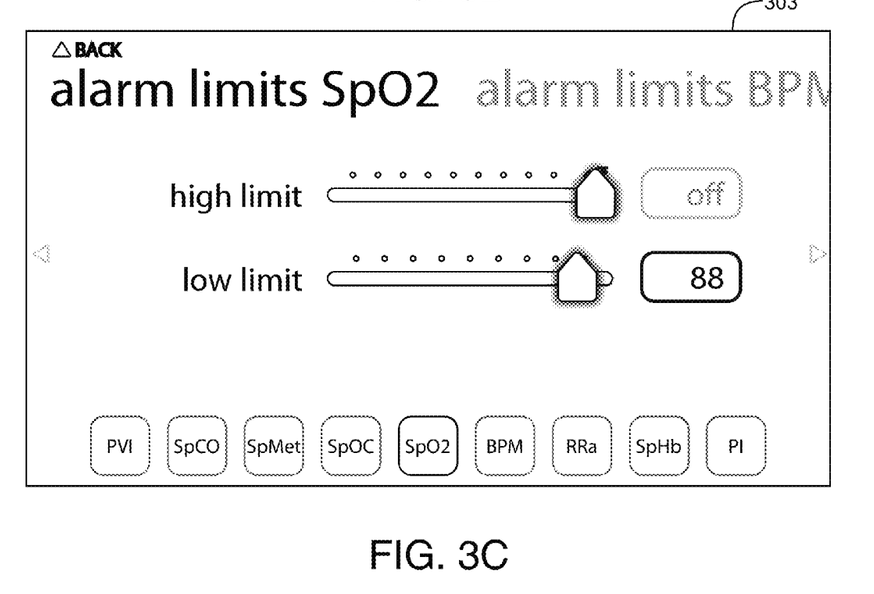

FIGS. 3A-C illustrate a physiological monitor main menu 301 (FIG. 3A) and sub-menus 302, 303 (FIGS. 3B-C) implemented with a scroller construct, as described above with respect to FIGS. 2A-D. For example, a user may touch "parameter settings" 310 in the main menu scroller 301 and be presented with a parameter menu stroller 302. The user may then touch "alarm limits" 320 in the parameter settings stroller 302 and be presented with the alarm limits scroller 303.

Figure 4A:
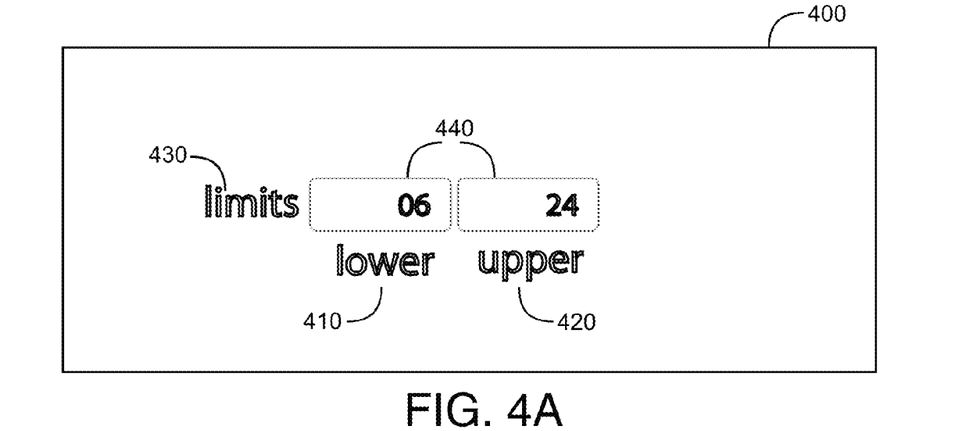
FIGS. 4A-C are illustrations of a spinner.
Figure 4B:
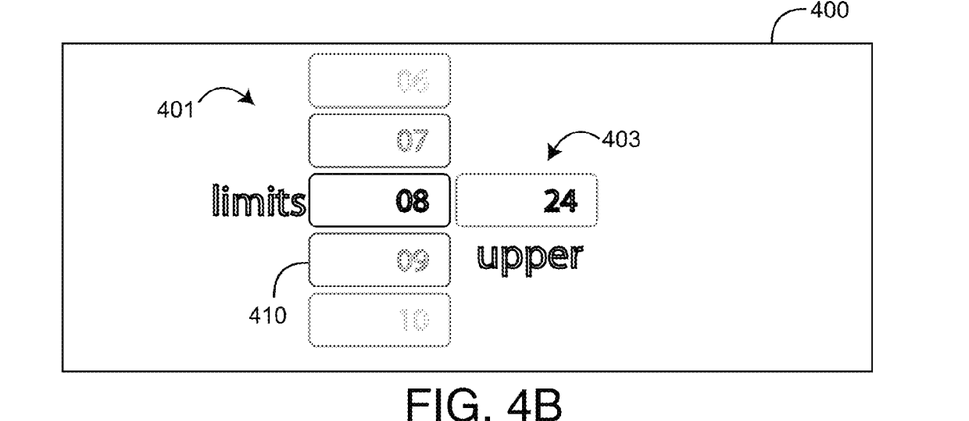
Figure 4C:
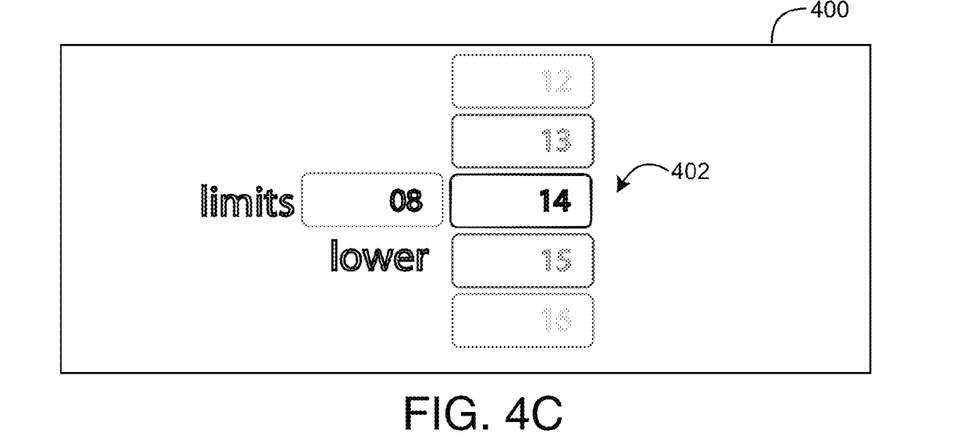

FIGS. 4A-C illustrate a spinner having one or more tiers, which open one at a time. Shown is a two-tiered spinner 400. Each spinner tier 410, 420 can display any specified number. The user applies touch to open one tier of the spinner at a time. The spinner elements include a label 430, buttons 440 and corresponding button text. A tier open state 401 (FIG. 4B), 402 (FIG. 4C) has two preceding and two trailing values on a spinner element, and a spinner closed state 403 (FIG. 4B) displaying the selected value. In the spinner open state, the user can use a vertical touch and move or flick to adjust the value. When open, a spinner tier overlays other user controls on the screen. To close the spinner the user can touch the center, highlighted value or another control on the screen.

Figure 5A:
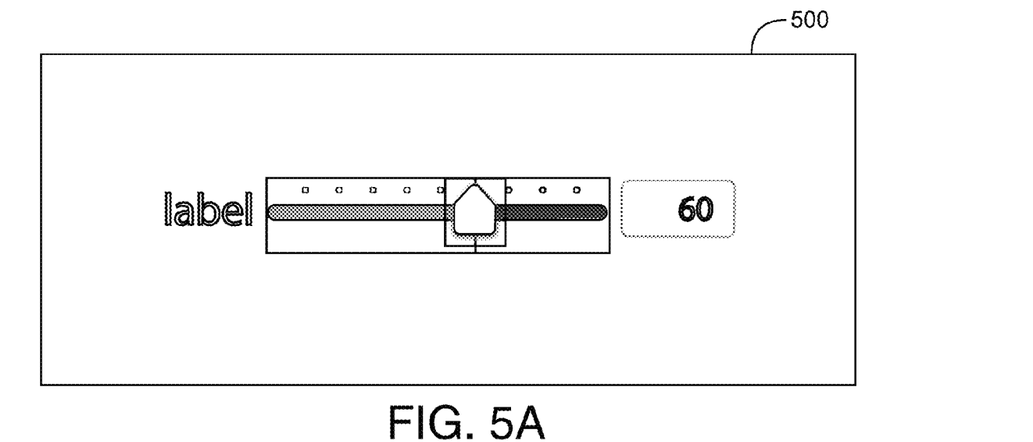
FIGS. 5A-B are illustrations of a slider.
Figure 5B:
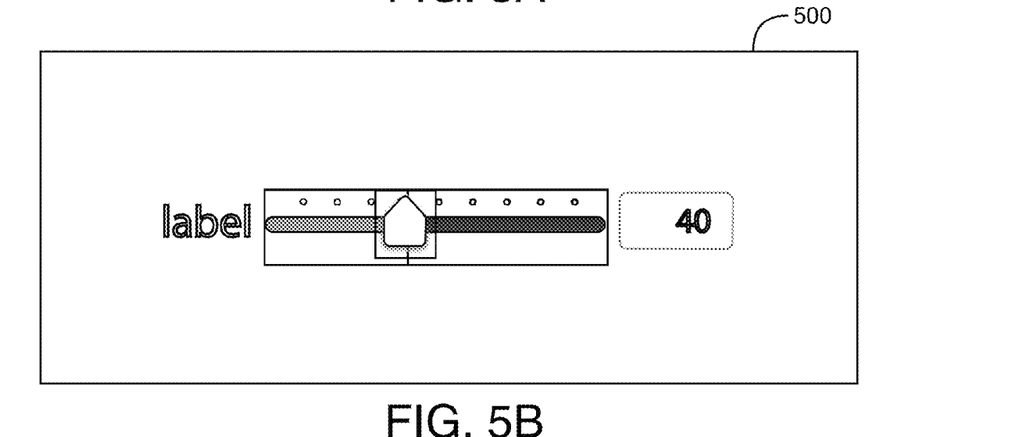
Figure 6:
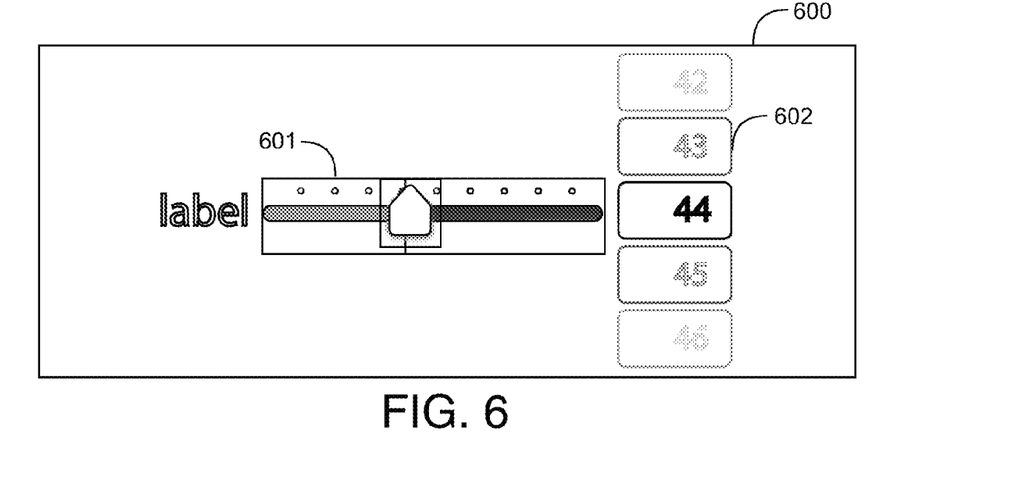

FIGS. 5A-B illustrate a slider 500 that allows one touch value settings, such as for parameter limits as one example. FIG. 6 illustrates a slider-spinner 600 embodiment, which is a combination of a slider and spinner, each described separately above. A slider-spinner 600 advantageously allows both a quick and an accurate capability to set a value. In particular, the slider 601 allows a user to quickly get to a specific range and the spinner allows a fine adjustment of that range.

Figure 7A:
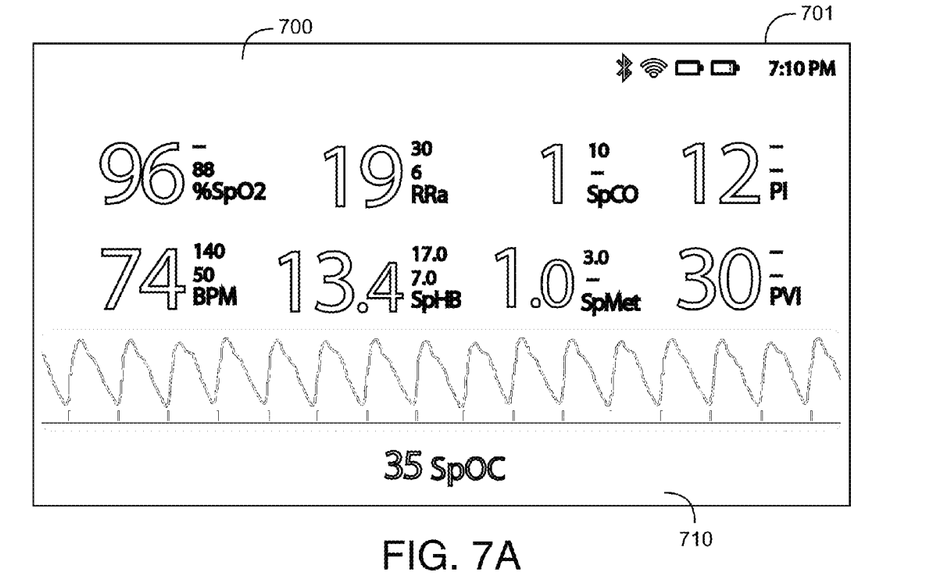
FIGS. 7A-D are illustrations of a parameter monitor touchscreen providing dynamic allocation of the parameter display area utilizing a parameter well.
Figure 7B:
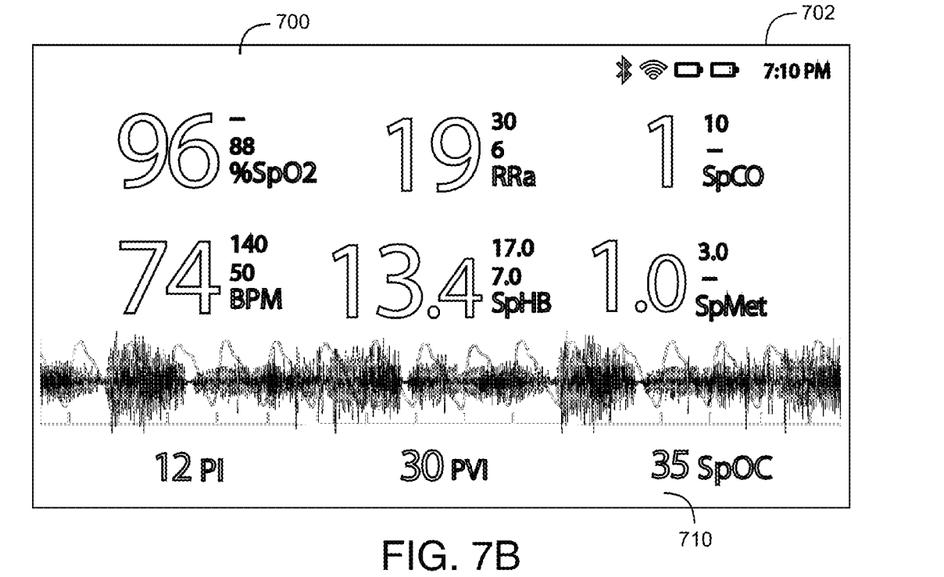
Figure 7C:
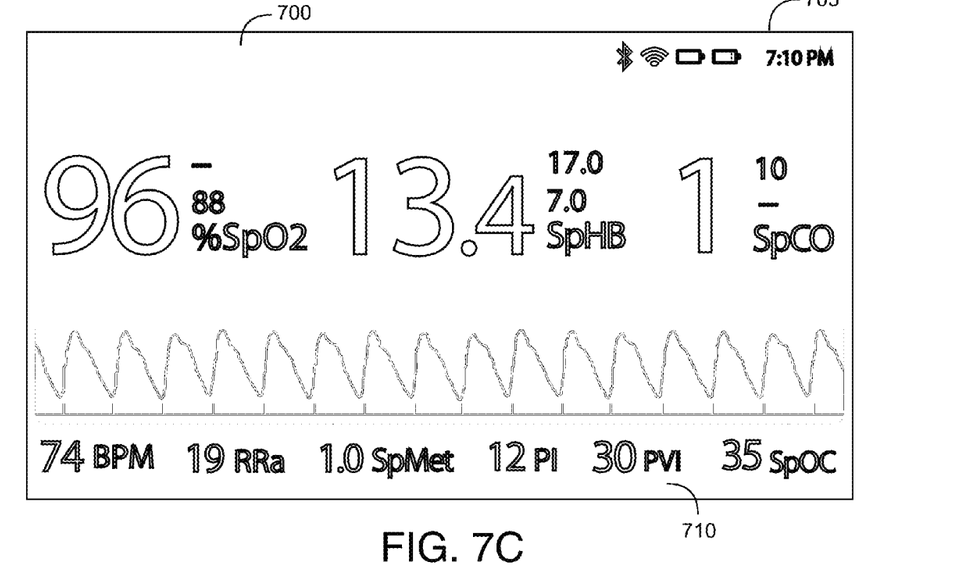
Figure 7D:
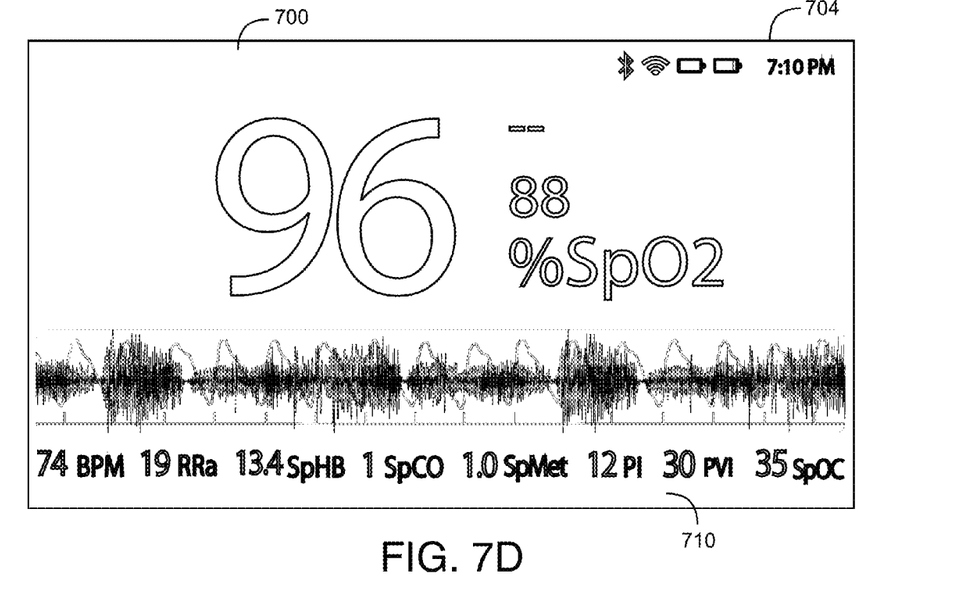

FIGS. 7A-D illustrate a scalable parameter display 700 and corresponding parameter well 710 advantageously providing a parameter monitor touchscreen with dynamic allocation of the parameter display area 700 so as to maximize screen capability and a caregiver's ability to automatically emphasize and distinguish parameters of greater importance from parameters of lesser importance. In particular, different monitor users care about different parameters. For example, a hemotologist might focus on blood-related parameters, such as SpHb, a noninvasive and continuous reading of total hemoglobin. Accordingly, the user has the ability to remove parameters of little or no interest from a main display area 700 and to place them in the parameter well 710. This is accomplished by a touch and hold gesture over a parameter to select the parameter, followed by a drag and drop gesture to remove the selected parameter from the main display area 700 into the well 710. The parameters remaining in the main display area 700 become bigger in size according to the number of remaining parameters. The removed parameters become smaller in size according to the number of parameters in the well 710. That is, the monitor dynamically adjusts parameter size according the available main display and well display areas. For example, FIG. 7A illustrates eight parameters in the main display 700 and one parameter (SpOC) in the well 710. FIG. 7B illustrates the relative size of six parameters in the main display 700, with three parameters in the well 710. FIG. 7C illustrates three parameters in the main display 700 dynamically increasing in size and six parameters in the well 710. FIG. 7D illustrates a single, very large SpO2 parameter advantageously solely displayed 700 so as to provide particular emphasis to that parameter and in a manner that can be seen across a room and readily noticed and monitored for change even by caregivers passing by at a distance. Sensors trigger parameters that are displayed so as not to hold space for non-active parameters.

A physiological monitor touchscreen interface has been disclosed in detail in connection with various embodiments. These embodiments are disclosed by way of examples only and are not to limit the scope of the claims herein. One of ordinary skill in art will appreciate many variations and modifications.

What is claimed is:

1. A physiological monitor touchscreen interface presents interface constructs on a touchscreen display that are particularly adapted to finger gestures so to change at least one of a physiological monitor operating characteristic and a physiological touchscreen display characteristic, the physiological monitor touchscreen interface comprising:
   a first interface construct operable to select a menu item from a touchscreen display wherein the first interface construct comprises:
      a first scroller that presents a rotating set of the menu items in a touchscreen display area wherein the first scroller presents a rotating set of second level menu items upon selection of the menu item; and
      a second scroller that presents a rotating set of thumbnails in a display well,
      wherein the thumbnails reference the menu items and the thumbnails rotate with the menu items;
   a second interface construct operable to define values for the selected menu item wherein the second interface construct is a slider for selecting limits for one of the second level menu items;
   a spinner used in conjunction with the slider for making a first gross limit selection with the slider followed by a finer limit selection with the spinner;
   a parameter area for displaying parameter values in a full presentation format;
   a parameter well area for displaying parameter values in an abbreviated presentation format, the full presentation format being a larger font than the abbreviated presentation format; and
   a dynamic space allocation for the parameter values presented in the parameter area such that the fewer parameters in the parameter area and, accordingly, the more parameters in the parameter well area, the larger the display font for the parameters in the parameter area.

2. A physiological monitor touchscreen interface method for customizing a physiological monitor comprising:
   defining a virtually rotating menu scroller;
   flicking a first icon on the menu scroller so as to spin the rotating menu;
   touching a second icon on the menu scroller so as to open a corresponding menu selection;
   synchronizing a thumbnail scroller with the menu scroller;
   touching a thumbnail within the thumbnail scroller so as to open a menu selection;
   touching and moving a slider so as to set a parameter value; and
   opening a spinner so as to refine the parameter value;
   wherein opening the spinner comprises opening a first tier of the spinner to define a first parameter limit.

3. The physiological monitor interface method according to claim 2 wherein opening the spinner comprises opening a second tier of the spinner to define a second parameter limit.

4. The physiological monitor interface method according to claim 3 further comprising scaling a plurality of parameters within a parameter display area by moving at least one of the parameters between the parameter display area and a parameter well area.

5. A physiological monitor touchscreen interface comprising:
   a first scroller means for virtually rotating a plurality of menu items under finger control across a parameter display area of a touchscreen display;
   a second scroller means for virtually rotating a plurality of thumbnail means within a parameter well area of the touchscreen display;
   the second scroller means rotating in response to the first scroller means.

6. The physiological monitor interface method according to claim 5 further comprising a slider means for grossly defining values for selected one of the menu items.

7. The physiological monitor interface method according to claim 6 further comprising a spinner means for finely defining values for the selected one of the menu items, where the spinner means is used in conjunction with the slider means.

8. The physiological monitor interface method according to claim 7 further comprising a scalable means for increasing the size of displayed parameters according to the number of displayed parameters.

9. The physiological monitor interface method according to claim 8 further comprising a parameter well means for removing parameters from a parameter display area so as to increase the size of the displayed parameters.

* * * * *